United States Patent
Kerr et al.

[11] Patent Number: 5,960,530
[45] Date of Patent: Oct. 5, 1999

[54] METHOD OF MAKING A SAMPLE LIQUID ASPIRATION AND DISPENSING PROBE

[75] Inventors: Alexander F. Kerr, Wappingers Falls; Nicholas F. DiDomenico, Pine Bush, both of N.Y.

[73] Assignee: Bayer Corporation, Tarrytown, N.Y.

[21] Appl. No.: 08/807,177

[22] Filed: Feb. 27, 1997

Related U.S. Application Data

[62] Division of application No. 08/299,049, Aug. 31, 1994, Pat. No. 5,639,426.

[51] Int. Cl.⁶ ..................................................... B23P 19/02
[52] U.S. Cl. .......................... 29/525; 29/522.1; 264/230
[58] Field of Search ................... 29/525, 522.1, 29/523, 447; 72/283; 264/230, 234, 346

[56] References Cited

U.S. PATENT DOCUMENTS

| | | |
|---|---|---|
| 2,270,398 | 1/1942 | Westin . |
| 3,546,916 | 12/1970 | Maeda et al. . |
| 4,007,639 | 2/1977 | Haeckel .............................. 73/425.4 P |
| 4,377,894 | 3/1983 | Yoshida .................. 29/421 R |
| 5,000,921 | 3/1991 | Hanaway et al. ........................ 422/100 |
| 5,045,286 | 9/1991 | Kitajima et al. ........................ 422/100 |
| 5,159,842 | 11/1992 | Palmer et al. ........................ 73/864.01 |
| 5,183,765 | 2/1993 | Qureshi et al. ........................... 436/180 |
| 5,218,875 | 6/1993 | Volpe et al. ......................... 73/861.01 |
| 5,485,667 | 1/1996 | Kleshinski ................................ 29/447 |
| 5,487,792 | 1/1996 | Fox ............................................ 72/43 |

*Primary Examiner*—P. W. Echols
*Assistant Examiner*—John C. Hong
*Attorney, Agent, or Firm*—Andrew L. Klawitter, Esq.; Rodman & Rodman

[57] ABSTRACT

The sample liquid aspirating and dispensing probe includes a tubular plastic inner member and a tubular metallic outer member. One or more sections of the plastic inner member are drawn-down in dies to provide a large diameter section, a small diameter section and an intermediate transition section. The plastic member is inserted in the metal member and annealed to conform the profile of the plastic member transition section with a streamlined transition section of the metal outer member. The dual member probe has an ultra-smooth interior surface, substantially free of eddy-forming imperfections. Thus there is minimal likelihood of turbulent eddies forming when rinse liquid is directed through the probe. The metallic member provides the probe with a conductive capability for capacitive liquid level sensing.

6 Claims, 5 Drawing Sheets

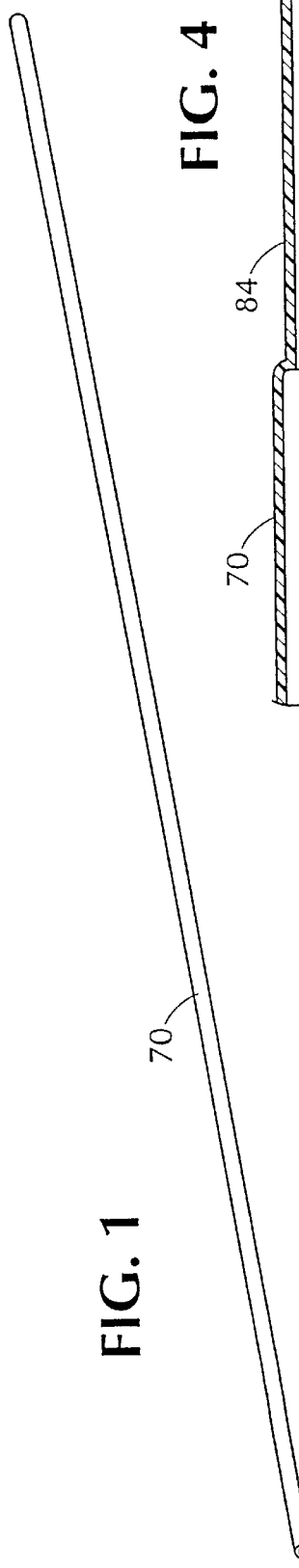
FIG. 1
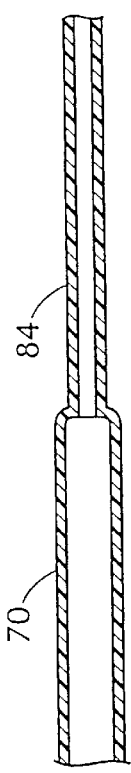
FIG. 2
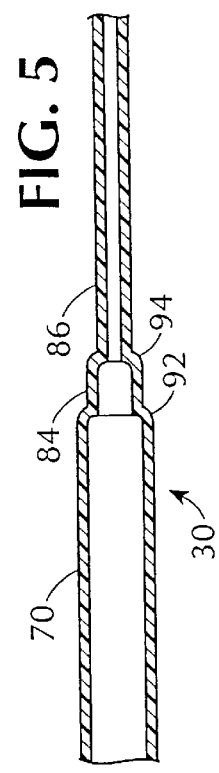
FIG. 4
FIG. 5
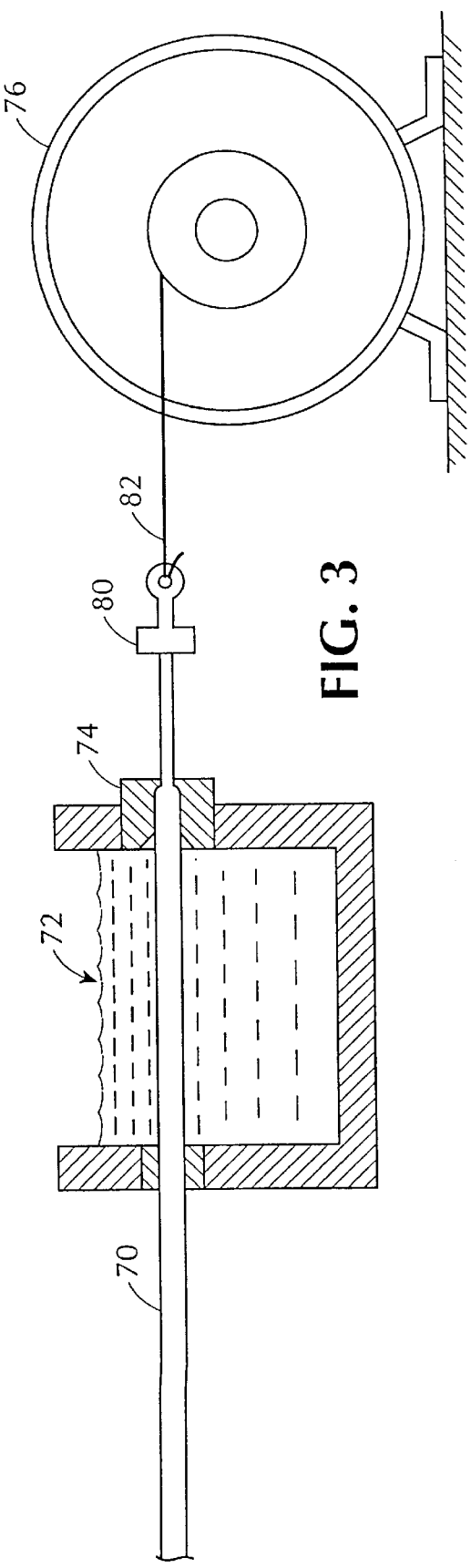
FIG. 3

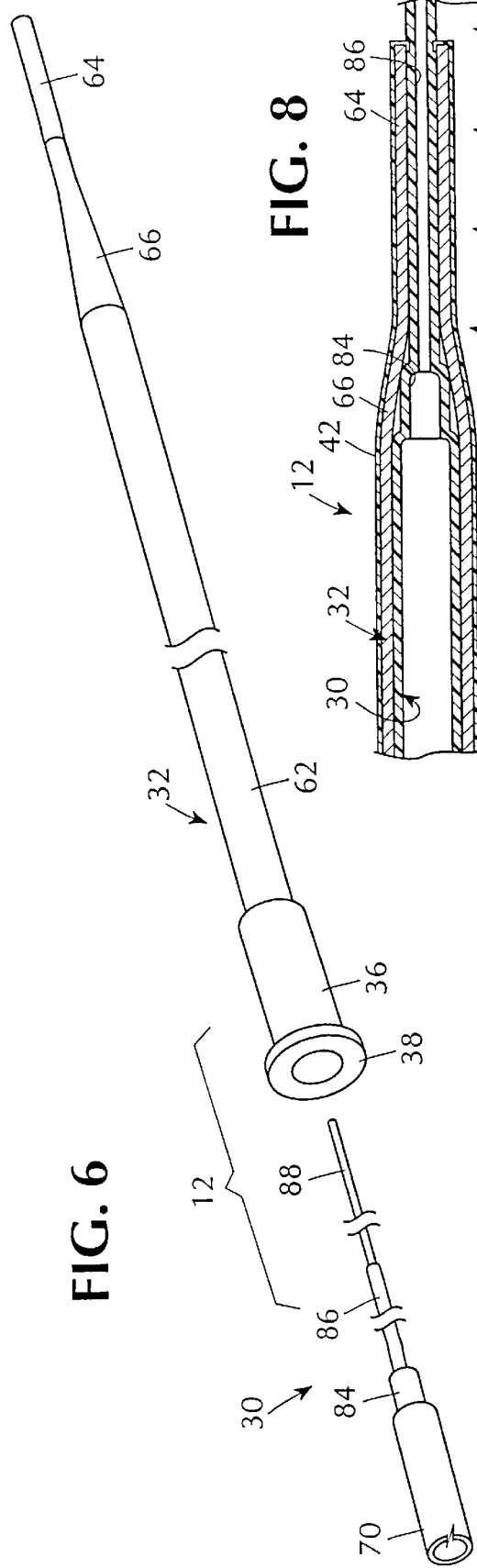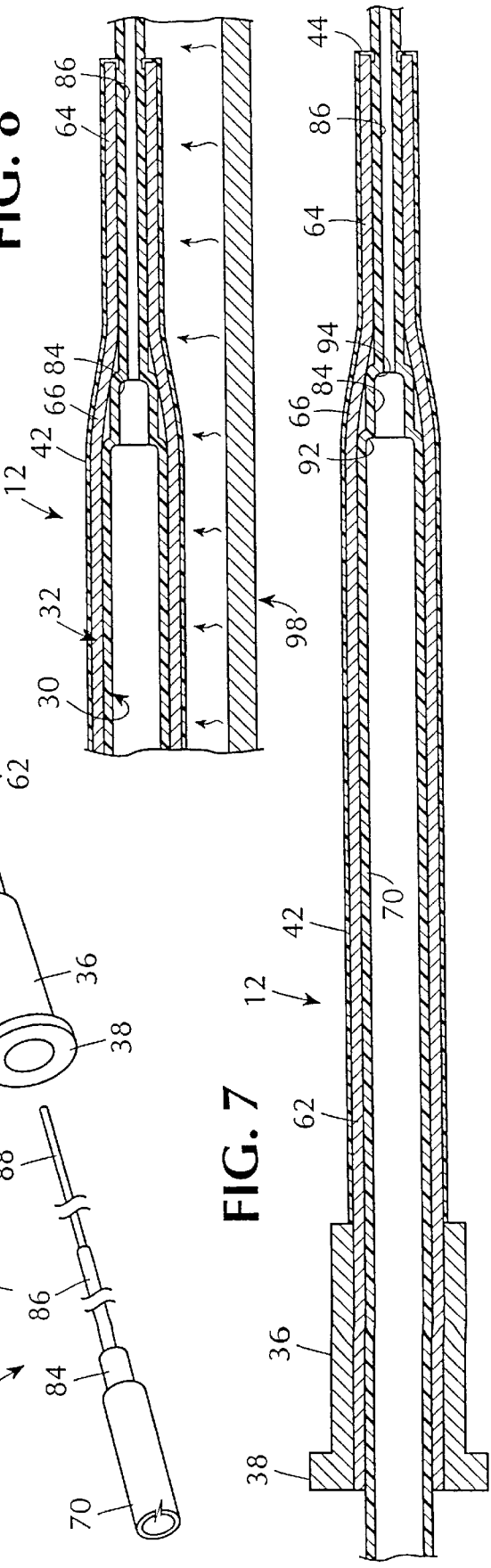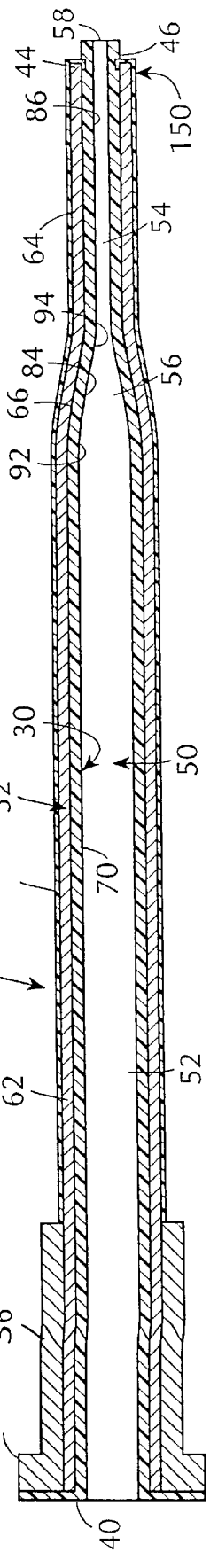

METHOD OF MAKING A SAMPLE LIQUID ASPIRATION AND DISPENSING PROBE

This is a division, of application Ser. No. 08/299,049, filed Aug. 31, 1994 now U.S. Pat. No. 5,639,426.

BACKGROUND OF THE INVENTION

This invention is directed to sample liquid aspiration and dispensing systems and more particularly to a novel conductive aspiration and dispensing probe for repetitive sample taking which has minimal carryover from previously aspirated and dispensed samples.

Samples of a liquid specimen such as serum that are to be tested or analyzed are usually drawn from a single source such as a sample tube. In immuno-assay testing of serum it is common practice to conduct four to six different tests and each test generally requires the drawing of a separate sample. The repetitive drawing of serum samples and the processing of such samples in the reagents used for testing can be extremely time-consuming if such tests are performed by a technician in a laboratory. Since the demand for immuno-acid serum testing has steadily increased it has become necessary to automate almost all aspects of such testing, including the repetitive drawing of samples.

An automated sampling system such as shown in U.S. Pat. No. 5,133,218 operates with a sampling probe that is used for repetitive sample taking. Carryover of sample and reagent from one aspiration to another is substantially reduced to acceptable limits by automatically rinsing the probe after each sample is aspirated and dispensed. Thus, the probe is relatively free of carryover during repetitive aspirations and dispensations of sample, even when such samples are taken from different sources such as different sampling tubes.

The probe of U.S. Pat. No. 5,133,218 is non-conductive and has at least two sections of different diameter. The junction between the sections of different diameter is often the site of turbulent eddies that form in the rinse liquid as it flows through the probe. Turbulent eddies interfere with the flushing action of the rinse liquid and thus reduce the effectiveness of a rinse cycle.

Other known aspirating and dispensing probes such as shown in U.S. Pat. No. 4,210,156; 4,707,337; 5,073,347; and 5,232,669 are generally formed by a molding process. However, a molded surface usually has imperfections or irregularities of the type that can cause the formation of turbulent eddies at almost any point along the inner surface of the probe when a rinse liquid flows through the probe.

It is also known to coat the inner surface of a probe, especially if it is formed of metal, with a plastic material to smooth out any imperfections in the molded surface. However, surface flaws in a plastic coating are common and will give rise to turbulent eddy conditions in rinse liquid that flows along the coated surface during a rinse cycle.

The drawing down of a plastic tube using dies is a preferred method for making a probe having two or more sections of different diameter since the draw-down process can be controlled to preserve the smoothness of the inner surface of the tube and such surface smoothness is superior to that of a molded or coated surface.

Surface smoothness in a die-drawn tube is usually fine enough to avert the formation of turbulent eddies in a current of rinse liquid. However, the junction between diametrical reductions in a die-drawn tube can be the site of turbulent eddy formation when rinse liquid flows past the junction.

It is thus desirable to provide a sample liquid aspirating and dispensing probe which has optimal inner surface smoothness and a streamlined profile to avert the formation of turbulent eddies when rinse liquid flows through the probe. It is also desirable to render such probe conductive to permit capacitive liquid level sensing.

OBJECTS AND SUMMARY OF THE INVENTION

Among the several objects of the invention may be noted the provision of a novel sample liquid aspirating and dispensing probe, a novel probe which has a large diameter section, a small diameter section and a streamlined transition between the large and small diameter sections, a novel probe which is conductive, a novel probe formed of die-drawn plastic tube and a metal sleeve, a novel probe having a die-drawn plastic tubular inner member and a metallic outer member in substantial surface to surface contact and a novel method of streamlining fluid flow through a probe.

Other objects and features of the invention will be in part apparent and in part pointed out hereinafter.

In accordance with the present invention, the sample liquid aspirating and dispensing probe includes an elongated tubular metallic member having a relatively large diametrical section and a relatively small diametrical section joined by a streamlined transition section that has the profile of a hollow frustum of a cone. A plastic tubular inner member is inserted into the tubular metallic outer member and has corresponding large and small diametrical sections and a corresponding transition section.

The tubular plastic inner member is formed by drawing down a plastic tube through at least two dies to provide at least two sections of different diameter. A step-like junction is defined between the two sections of different diameter. An intermediate draw-down can be used to form a transition section between the large and small diameter sections. The transition section defines one or more step-like junctions between the large and small diameter section. Such junctions can be the site of turbulent eddies when rinse liquid passes along the transition section.

The drawn-down plastic tube with the step-like transition section is inserted in the metal tube, which has a streamlined transition section between the metal sections of different diameter. The plastic tube is pulled or otherwise positioned in the metal tube to align the transition section of the plastic tube with the transition section of the metal tube. The metal and plastic tube assembly is then heated to anneal the plastic tube. Annealing reestablishes the memory of the plastic tube to enable the profile of the transition section of the plastic tube to conform to the profile of the transition section of the metal tube. In this manner the streamlined profile of the metal tube transition section influences the shape of the transition section of the plastic tube and enables the plastic tube to assume the form of the streamlined profile of the outer metal tube.

Streamlining the profile of the transition section of the plastic tube, which already has ultra-smooth surface characteristics, provides a flow passage that substantially eliminates areas of potential turbulence. Thus, rinsing liquid that is flushed through the probe can provide effective cleaning action through the plastic transition section as well as through the plastic sections of different diameter, thereby minimizing the possibility of carryover.

The invention accordingly comprises the constructions and method hereinafter described, the scope of the invention being indicated in the claims.

DESCRIPTION OF THE DRAWINGS

In the accompanying drawings,

FIG. 1 is a simplified perspective view of plastic tubing that is used to form the plastic component of the probe;

FIG. 2 is a sectional view thereof, taken through the longitudinal axis of the tubing;

FIG. 3 is a simplified schematic view of a tube drawing apparatus for drawing down the diameter of the tube;

FIG. 4 is an enlarged fragmentary sectional view of the plastic tube of FIG. 1 after one section of the tube has been drawn down through a die;

FIG. 5 is a view similar to FIG. 4 showing a drawn-down tube with a large diameter section, a small diameter section and a transition section;

FIG. 6 is a simplified perspective exploded view of the plastic tubular component and the metal tubular component of the probe prior to assembly;

FIG. 7 is a sectional view thereof after the plastic and metal components have been assembled;

FIG. 8 is a fragmentary sectional view of the assembly of FIG. 7 during an annealing operation;

FIG. 9 is a sectional view thereof after the annealing operation has been completed;

Corresponding reference characters indicate corresponding parts throughout the several views of the drawings.

DETAILED DESCRIPTION OF THE INVENTION

Figure 14:
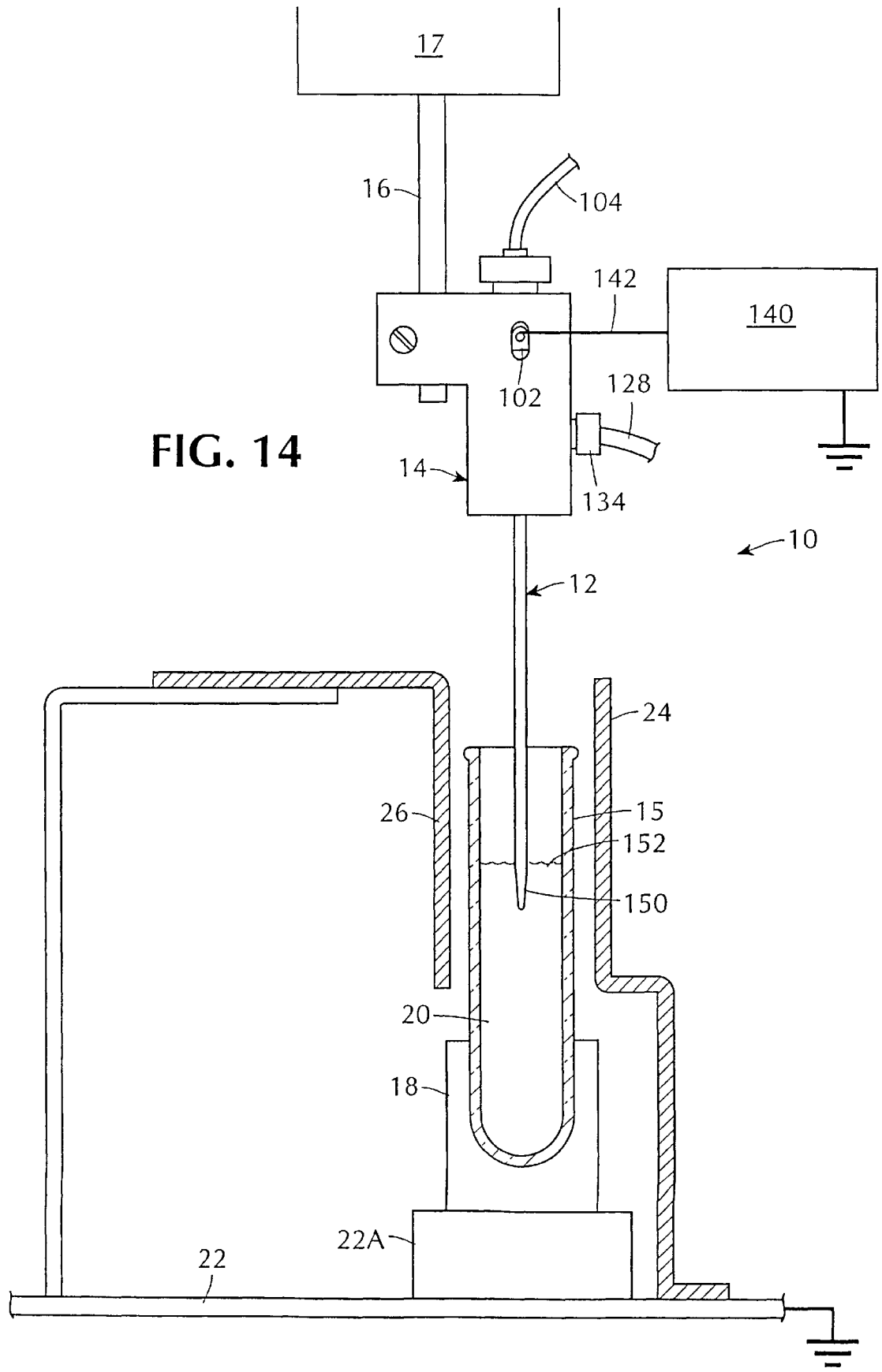
FIG. 14 is a simplified schematic view of an aspiration and dispensing system that incorporates the present invention.

An aspiration and dispensing system incorporating one embodiment of the present invention is generally indicated by the reference number 10 in FIG. 14. The system 10 includes an aspiration and dispensing probe 12 extending downwardly from a support head 14. The support head 14 is connected to a rod 15, that is moveable upwardly and downwardly, backward and forward, and side to side in a known manner by a known drive arrangement schematically indicated at reference number 17.

The probe 12 is thus moveable into and out of a sample tube 15 that is supported in a sample tube tray 18 disposed below the probe 12. The sample tube tray 18 supports a row of similar sample tubes 15. Each of the sample tubes 15 contains a liquid sample 20 such as serum. The tray 18 is disposed on racks 22a on a support surface 22.

A pair of spaced, elongated capacitor plates 24 and 26 are disposed on opposite sides of the sample tube tray 18. The plates 24 and 26 are configured to allow the racks 22a, the tray 18 and the sample tubes 15 supported by the tray 18 to be moved relative to the capacitor plates 24 and 26 to align selected sample tubes 15 with the probe 12. Movement of the tray 18 is accomplished in any suitable known manner.

Referring to FIG. 9, the probe 12 includes an inner plastic tubular component 30 preferably formed of a tetrafluoroethylene fluorocarbon resin such as sold under the designation Teflon®, and an outer metal tubular component 32 preferably formed of brass. A metal securing collar 36, also formed of brass and having a flange 38, is joined to an end portion 40 of the probe 12. A Teflon® coating 42 is provided on the outer surface of the metal tube 32, extending from the securing collar 36 to a free end 44 of the metal tube 32, and slightly inside the free end 44.

The metal tube 32 is formed in any suitable known manner, such as by swaging, and includes a large diameter section 62, a small diameter section 64, and a transition section 66. The transition section 66 of the metal tube 32 is in the shape of a hollow frustum of a cone and provides a relatively streamlined transition from the large diameter section 62 to the small diameter section 64.

The plastic tube 30 is formed from commercially available tube stock 70, as shown in FIGS. 1 and 2. The tube stock 70 has a fixed, uniform inside diameter along the entire length, such as approximately 0.061 inches inside diameter and approximately 0.083 inches outside diameter.

The tube 70 is drawn down through one or more dies in several stages. Each drawn-down stage is intended to reduce the inside and outside diameter by a predetermined amount. The draw-down process is preferable to a mandrel squeezing process because in any type of squeezing process, surface imperfections will appear on the inside of the tube, such as pitting, crimping or creasing. These surface imperfections can cause turbulent eddies during a rinse cycle and are thus a potential site for carryover material. The draw-down process can be controlled to have minimal effect on altering the ultra-smooth inside surface characteristics of the tube 70.

During the draw-down process the tube 70, in accordance with known techniques, is drawn through a die 74 preceded by a heated oil bath 72 (FIG. 3). The tube 70 is pulled through the die 74 in any suitable known manner, as by a pull wheel 76 driven by a low speed motor (not shown). A clamp 80 and a cable 82 connect one end of the tube 70 to the pull wheel 76.

The tube 70 is pulled a predetermined amount to provide the first draw-down condition 84, as shown in FIG. 4. A second die (not shown) is interchanged with the die 74 to provide the tube 70 with a further draw-down 86, as shown in FIG. 5. The draw-down section 84 is thus a transition section between the sections 70 and 86. A further draw-down 88, as shown in FIG. 6, can be furnished to facilitate insertion of the resulting plastic tubular component 30 within the metal tube 32, as shown in FIG. 6, and provide a tail for pulling the plastic tube 30 through the metal tube 32.

During the draw-down process a shoulder or step 92 is formed in the tube stock 70 in advance of the transition section 84 and a shoulder or step 94 is formed in the transition section 84 in advance of the drawn-down section 86. The shoulders 92 and 94, although shown in exaggerated fashion in FIG. 5, can be the site of local eddies of turbulence that form when rinse fluid is flushed through the tube 30. The rinsing action at the shoulders 92 and 94 is thus not as optimum as a laminar flow rinse condition that normally prevails along the nonshouldered sections 70 and 86 of the tubular component 30. Turbulent eddy conditions at the shouldered sections 92 and 94 thus reduce the overall effectiveness of the rinsing of the probe 12.

The outer dimensions of the tubular plastic component 30 closely correspond with the inner dimensions of the metal tubular component 32. For example, the nominal inner diameter of the tube stock 70 before the draw-down is approximately 0.061 inches and the nominal outer diameter is approximately 0.083 inches. The transition section 84 of the tube 30 as shown in FIGS. 5–8 has an inner diameter of approximately 0.030 inches and an outer diameter of approximately 0.050 inches. The length of the transition section 84 as shown in FIG. 9 is approximately 0.200 inches. The drawn-down section 86 of the plastic tubular component 30 has a nominal inner diameter of approximately 0.021 inches and a nominal outer diameter of approximately 0.041 inches. The drawn-down tail section 88 of the plastic tubular component 30 has a nominal inner diameter of approximately 0.021 inches and a nominal outer diameter of approximately 0.037 inches.

The metal tube 32 has an overall length from one end to the other of approximately 5.2 inches. The section 64 of the metal tube has a nominal inner diameter of approximately 0.040 inches and a nominal outer diameter of approximately 0.058 inches. The length of the section 64 is approximately 0.300 inches. The transition section 66 has an angle of inclination to the longitudinal axis of the tube 32 of approximately 23°. The length of the transition section is approximately 0.34 inches. The section 62 of the metal tube 32 has a nominal inner diameter of approximately 0.081 inches and a nominal outer diameter of approximately 0.093 inches.

The drawn-down tail section 88 of the plastic tube 70 is sufficiently long to permit insertion through the entire length of the metal tube 32. The drawn-down tail section 88 thus extends beyond the free end 44 of the metal tube and can be pulled away from the free end to facilitate insertion of the plastic tube 30 in the metal tube 32 in the manner shown in FIG. 7.

As most clearly shown in FIG. 7, the nonreduced tube stock portion 70 of the plastic tubular component 30 corresponds to the large diameter section 62 of the metal tube 32. The drawn-down transition section 84 of the plastic tubular component 30 corresponds to the transition section 66 of the metal tube 32. The drawn-down small diameter section 86 of the plastic tube component 30 corresponds to the small diameter section 64 of the metal tube 32.

The plastic tubular component 30 when inserted in the metal tubular component 32, provides a probe 12 with conductive capability and an ultra-smooth interior surface.

However, it is desirable to eliminate the shouldered sections 92 and 94 of the plastic tubular component 30 to provide a streamlined transition section between the plastic sections 70 and 86. The probe assembly of FIG. 7 is thus annealed, as shown schematically in FIG. 8, by, for example, heating the assembled tubes 30 and 32 for 1 hour at 150° C. in any suitable known annealing apparatus 98.

Annealing the plastic tube component 30 causes the transition section 84 to relax against the transition section 66 of the metal tube 32. The plastic transition section 84 is thus enabled to conform to the profile of the metal transition section 66 as show in FIG. 9. During annealing of the plastic tube 30, the outer metal tube 32 functions as a mold for reforming the plastic transition section 84 to a desirable streamlined profile without altering the surface characteristics of the inner surface of the plastic tube 32. With the plastic transition section 84 in surface conformity with the metal transition section 66, the plastic shoulders 92 and 94 of FIGS. 7 and 8 are eliminated and replaced by the streamlined plastic intersections 92 and 94 of FIG. 9. The plastic transition section 84 of the probe 12 in FIG. 9 tapers from the section 70 to the section 86 and has the shape of a hollow frustum of a cone.

The streamlined inner surface structure of the plastic tube 30 at the transition section 84 substantially eliminates the likelihood that turbulent eddy flow conditions will arise in the probe 12 of FIG. 9.

An inner passageway 50 of the probe 12 is thus defined by the inside surface of the plastic tubular component 30 and extends from the end portion 40 to a free end 46. The free end 46 of the plastic tube 30 extends beyond the free end 44 of the metal tube a predetermined amount such as approximately 0.020 inches. The passageway 50 has a large diameter section 52 defined by the inner surface of the plastic section 70, a small diameter section 54 defined by the inner surface of the plastic section 86, and a transition section 56 between the sections 52 and 54 defined by the inner surface of the plastic transition section 84.

Figures 10, 11:
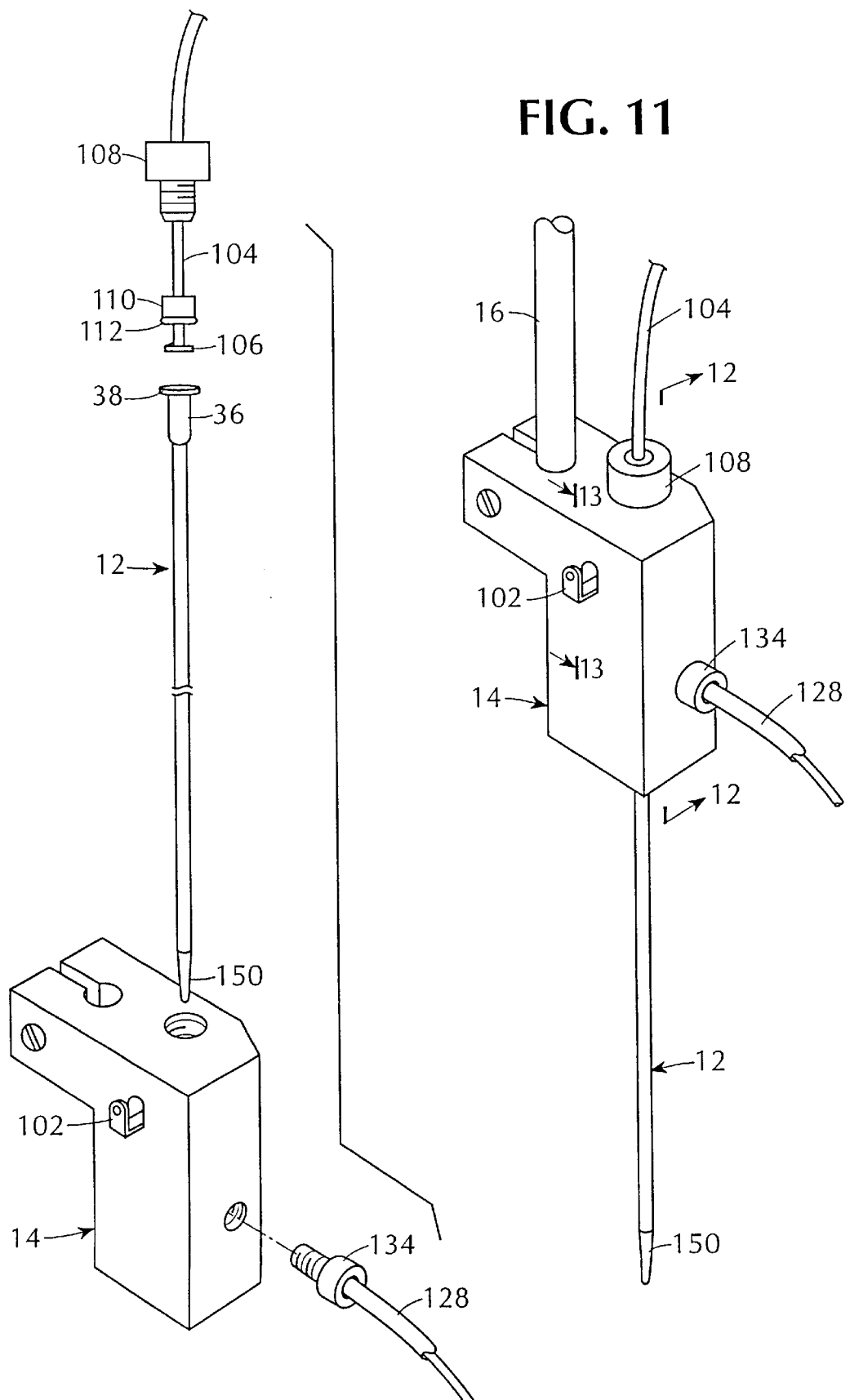
FIG. 10 is a simplified exploded perspective view of the probe and a support head for the probe.
FIG. 11 is an assembly view thereof.
Figures 12, 13:
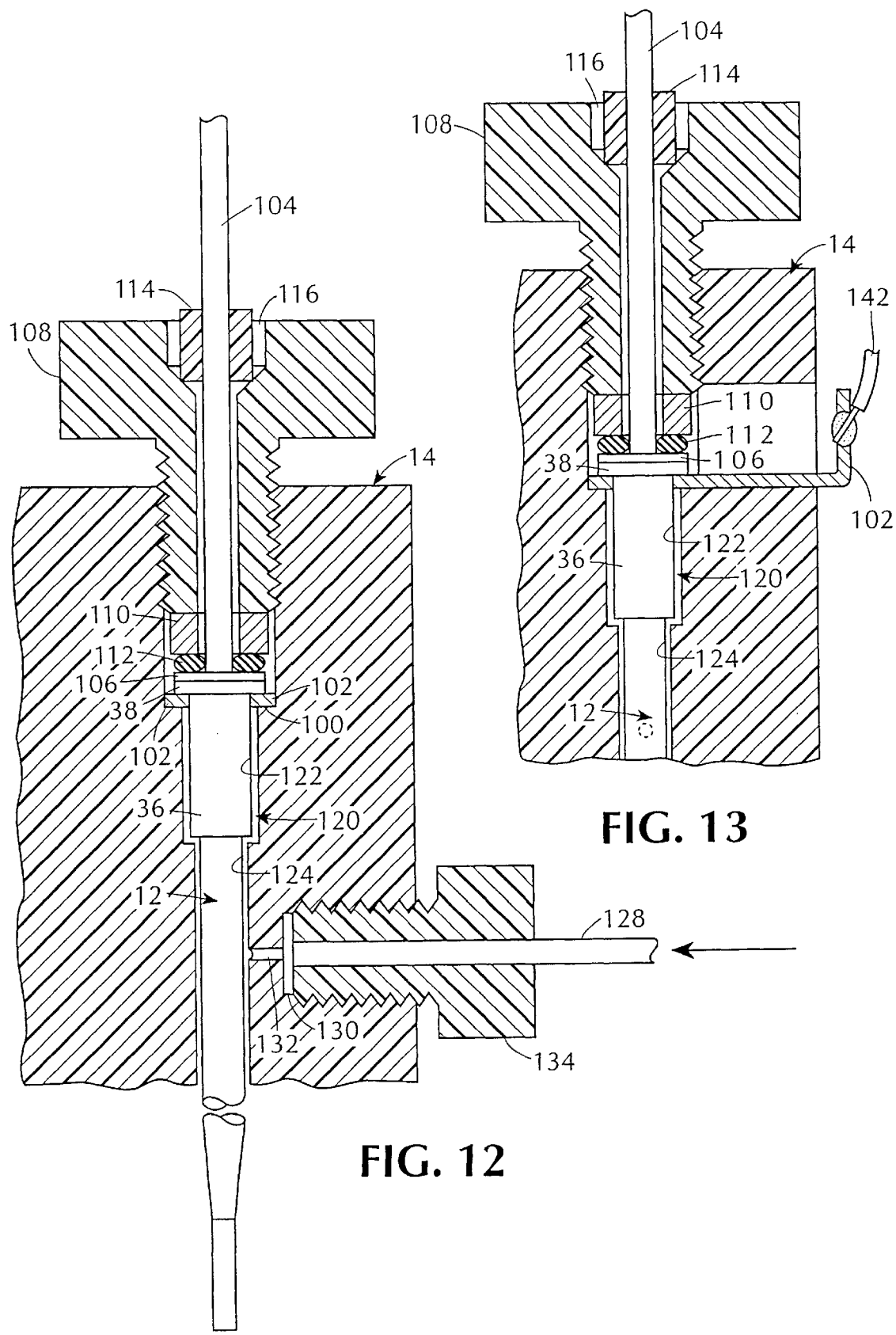
FIG. 12 is a sectional view taken on the line 12—12 of FIG. 11.
FIG. 13 is a sectional view taken on the line 13—13 of FIG. 11.

The probe 12 of FIG. 9 is assembled to the support head 14 in the manner shown in FIG. 10. The metal collar 36 of the probe 12 is encircled by an electrical contact terminal 102 that is sandwiched between a ledge 100 of the support head 14 (FIG. 12) and the metal flange 38. A conductor 142 establishes electrical communication between the electrical contact 102 and a power source 140 (FIG. 14). Thus electrical power can be provided to the probe 12 from the power source 140.

A flexible, elongated plastic connection tube 104, having an end flange 106, is compressed against and sealed to the metal flange 38 of the probe 12 by a threaded lock member 108, which urges a grommet 110 and an O-ring 112 against the flange 106. A plug member 114 is pressed into a recess 116 of the lock member 108 to stabilize the plastic tube member 104 relative to the lock member 108.

The probe 12 extends through a stepped bore 120 in the support head 14. The bore 120 includes a collar receiving section 122 and an oil section 124.

An oil tube 128 (FIG. 12) has an end flange 130 that is pressed against an oil feed port 132 that communicates with the oil channel 124. A threaded lock member 134 locks the oil tube 128 to the support housing 14.

In operation of the aspiration and dispensing system 10 the drive arrangement 17 and support rod 16 raise and lower the support head 14 and the probe 12 relative to a selected sample tube 15.

Prior to aspiration of serum 20 from the sample tube 15, a coating of oil, such as a known inert fluorocarbon oil compatible with Teflon® plastic, is coated onto the interior and exterior surface of the probe 12. The surface energy of the oil is substantially the same as the surface energy of Teflon plastic to permit preferential wetting of the plastic surface.

The probe 12 is coated with oil is in a manner similar to that disclosed in U.S. Pat. No. 5,133,218 wherein oil is aspirated into the probe 12 followed by aspiration of a small air segment (not shown). As the oil is drawn into the probe 12 followed by the air segment, the air segment forces the oil to the inside plastic surface of the probe to coat a thin layer of oil on the inner surface.

The outer Teflon-coated surface of the probe is coated with oil in a known manner from the oil feed port 132. Thus, when the serum is aspirated through the probe 12, it is surrounded by oil.

The probe 12 aspirates a predetermined amount of serum 20 from the sample tube 15 at a tip portion 150 of the probe 12. The support head 14 and the probe 12 are then elevated to clear the sample tube 15 and the capacitor plates 24 and 26. The probe 12 with aspirated serum is moved toward a test and analysis station (not shown) for dispensation of the aspirated serum at a desired reagent location.

After the aspirated serum is dispensed at a test site, the support head 14 and the probe 12 are moved in a known manner to a rinse station (not shown). At the rinse station, a known rinse liquid including water and a surfactant is pumped through the interior passage 50 of the probe 12 to flush out any remaining serum, as well as oil.

The rinse station is of known structure and operation and is designed such that the flow of rinse liquid from the inside of the probe strikes a rinse cup with a circular or concave surface (not shown) near the base of the probe. As the rinse liquid hits the concave surface, it is reflected upwardly from the rinse cup to effectively scrub the outside of the probe. The rinse procedure is in accordance with known techniques and does not form any part of the present invention.

When the rinsing cycle is completed, the support head 14 and the probe 12 are moved to an oil station to coat the inside surface of the probe as well as a portion of the outside surface with oil.

If the probe 12 is flush cut wherein the free end 46 of the plastic tube 30 is cut evenly with the free end 44 of the metal tube 32, there is a tendency for oil to occlude the opening 58 (FIG. 9) of the probe. By projecting the free end 46 of the plastic tube 30 from the free end 44 of the metal tube 32, it has been found that oil does not normally occlude the opening 58 of the probe 12, but tends to migrate toward the edges of the opening, thus leaving the opening 58 free of oil. Under this arrangement, aspiration of the serum sample can be accomplished with little or no aspiration of oil.

When the plastic free end portion 46 of the tube 30 projects from the metal free end portion 44 by as little as 0.020 inches, such projection also functions as a safety shock absorber should the probe 12 inadvertently bump against any surface. Preferably, the plastic free end portion 46 of tube 30 projects a predetermined axial distance from the metal free end portion 44 in the range of 0.015 to 0.025 inches.

Automatic aspiration of a predetermined, precise amount of serum 20 from the sample tube 15 is facilitated by detecting and signaling when the probe 12 enters the serum 20. It is thus necessary to ascertain the relative positions of the probe tip 150 and the level 152 of the serum 20 in the sample tube 15. Such detection is accomplished using a capacitive liquid level sensing system that is shown in simplified schematic form in FIG. 14.

When the capacitive liquid level sensing system ascertains a desired aspiration position of the probe tip 150 relative to the serum level 152 in the sample tube 15, the sensing system provides a sensor signal to initiate aspiration of a sample of the serum 20 from the sample tube 15 into the probe 12.

Operation of the capacitive liquid level sensing system requires that the sample tubes 15 and the sample tube support tray 18 be constructed of electrically nonconductive dielectric material. Although the probe 12 includes an electrically conductive metal tube 32, the interior and exterior surfaces of the tube 32 are covered with plastic. Thus the metal surface of the metal tube 32 is not exposed and there is no direct contact between the metal structure of the probe 12 and the serum 20 in the sample tube 15.

The spaced capacitor plates 24 and 26 constitute one electrode of the capacitor and the metal tube 32 of the probe 12, especially the tip portion 44, constitutes a second electrode of the capacitor. The amount of capacitance of the capacitor is dependent on the amount of dielectric material disposed between the electrode represented by the capacitor plates 24 and 26 and the electrode represented by the tip portion 44 of the metal tube 32.

The amount of serum 20 in the sample tube 15 also affects the amount of capacitance. In addition, the position of the metal tip portion 44 of the probe 12 relative to the liquid level 152 and relative to the capacitor plates 24 and 26 affects the amount of capacitance between the two electrodes.

As the metal tip 44 of the probe 12 moves downward towards the surface 152 of the serum 20 in the sample tube 15 the capacitance increases. The capacitance further increases upon penetration of the metal tip 44 into the serum 20. Capacitance readings thus serve to measure the relative position of the metal tip 44 and the serum surface 152, including depth penetration of the metal tip 44 into the serum 20. The increase in capacitance as the metal tip 44 enters the serum 20 is used to signal the aspiration cycle wherein a predetermined duration of aspiration draws in a predetermined amount of serum 20 into the probe 12.

Some advantages of the present invention evident from the foregoing description include a two-piece probe formed of plastic and metal. The plastic member via an annealing process has a transition section shaped by the transition section of the metal member. Since the metal member has a streamlined profile, the inner plastic member acquires a similar streamlined profile during annealing of the probe. A further advantage is that the plastic inner member, since it is drawn rather than molded, has an ultra-smooth surface that is substantially free of crimps, pits or other surface imperfections that can occur in a molding operation.

The small diameter plastic section 86 of the probe 12 permits precise control of a minimal amount of sample that is drawn into the probe. Minimal sample usage also permits optimum rinsing of the probe 12 with the smallest volume of rinse material.

Still another advantage is that the insertion of the plastic tube in the metal tube provides the probe with a conductive capability that facilitates liquid level sensing during the aspiration and dispensing process. A still further advantage of the invention is that the disposition of capacitor plates alongside the sample tubes permits free movement of the sample tubes relative to the probe. The capacitor plates and probe also provide a convenient means for measuring capacitance and sensing the liquid level of serum in the sample tube relative to the probe.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A method of making an aspiration and dispensing probe comprising,
    a) forming a hollow plastic inner member with first and second longitudinal sections of different diameter joined by plastic transition section that reduces the diameter of the inner member from the first longitudinal section to the second longitudinal section,
    b) forming a hollow metallic outer member with first and second longitudinal sections of different diameter joined by a metal transition section in the shape of a hollow frustum of a cone,
    c) sizing the outside and inside members to permit disposition of the inner member in the outer member such that the respective first and second sections of each member are in substantially coextensive surface-to-surface contact and the respective transition sections are longitudinally aligned, d) assembling the plastic members, and e) annealing the inner plastic member to temporarily soften the plastic member to enable the plastic transition section to confirm with the metal transition section in substantially coextensive surface-to surface contact between the respective transition sections.

2. The method of claim 1 wherein the step of assembling includes pulling the inner plastic member inside the outer metal member such that the first transition section is forced against the second transition section.

3. The method of claim 1 wherein the inner plastic member is cut at a free aspiration end to extend slightly beyond a corresponding free end of the metal outer member.

4. The method of claim 1 wherein the step of forming the sections of different diameter of the plastic inner-member is accomplished by drawing one or more selected portions of the plastic inner member through one or more corresponding selected dies.

5. The method of claim 1 wherein the inner plastic member is formed of polytetrafluoroethylene.

6. The method of claim 1 wherein the outer surface of the metal member is coated with polytetrafluoroethylene.

* * * * *

UNITED STATES PATENT AND TRADEMARK OFFICE
CERTIFICATE OF CORRECTION

PATENT NO : 5,960,530
DATED : October 5, 1999
INVENTOR(S) : Alexander F. KERR et al It is certified that error appears in the above-identified patent and that said Letters Patent is hereby corrected as shown below:

In column 3, line 48, change "15" to --16--.

In column 8, line 58, after "by" insert --a--.

In column 9, line 4, after "plastic" insert --and metal--.

In column 9, line 7, change "confirm" to --conform--.

Signed and Sealed this

First Day of August, 2000

Attest:

Q. TODD DICKINSON

Attesting Officer          Director of Patents and Trademarks

UNITED STATES PATENT AND TRADEMARK OFFICE
CERTIFICATE OF CORRECTION

PATENT NO.    : 5,960,530
DATED         : October 5, 1999
INVENTOR(S)   : Alexander F. Kerr et al.

It is certified that error appears in the above-identified patent and that said Letters Patent is hereby corrected as shown below:

Column 3,
Line 48, change "15" to -- 16 --.

Column 8,
Line 58, after "by" insert -- a --.

Column 9,
Line 4, after "plastic" insert -- and metal --.
Line 7, change "confirm" to -- conform --.

Signed and Sealed this

Fourth Day of September, 2001

*Attest:*

NICHOLAS P. GODICI
*Attesting Officer*    *Acting Director of the United States Patent and Trademark Office*